United States Patent [19]

Martin

[11] Patent Number: 4,503,846
[45] Date of Patent: Mar. 12, 1985

[54] DEROTATION LEG BRACE

[75] Inventor: Kelsey Martin, Azle, Tex.

[73] Assignee: Medical Designs, Inc., Azle, Tex.

[21] Appl. No.: 511,265

[22] Filed: Jul. 6, 1983

[51] Int. Cl.$^3$ .............................................. A61F 3/00
[52] U.S. Cl. ..................................... 128/80 C; 128/88
[58] Field of Search ................ 128/80 R, 80 C, 87 R, 128/83, 89 R, 80 F, 88; 2/22, 24

[56] References Cited

U.S. PATENT DOCUMENTS

| | | | |
|---|---|---|---|
| 3,581,741 | 6/1971 | Rosman et al. | 128/80 C |
| 4,144,592 | 3/1979 | Larson | 128/80 C X |
| 4,271,831 | 6/1981 | Deibert | 128/80 C |
| 4,381,768 | 5/1983 | Erichsen et al. | 128/80 C |
| 4,387,709 | 6/1983 | Shen | 128/87 R |

Primary Examiner—John D. Yasko
Attorney, Agent, or Firm—Wofford, Fails & Zobal

[57] ABSTRACT

A knee brace for alleviating problems with tibia rotation and tibia desubluxation with respect to a femur of a wearer and including conventional first and second pairs of elongate braces having their respective hinges connected at their central ends and having conventional straps and harness for adjustably placing and holding the respective pairs of elongate braces and hinges at a desired attained position; characterized by the improvement comprising an anterior cuff connected with a second pair of braces below the hinges and adapted to firmly engage the leg at the inside anterior of the tibia with a padded flattened chord for preventing rotation of the tibia. In a preferred embodiment, the knee brace also includes a posterior cuff connected with the first pair of braces and adapted to engage the posterior portion of the thigh posteriorly of the femur for also preventing desubluxation of the tibia with respect to the femur. Straps are provided for respectively holding the anterior and posterior cuffs close engagement with their respective distal and proximal members of the leg.

7 Claims, 5 Drawing Figures

DEROTATION LEG BRACE

FIELD OF THE INVENTION

This invention relates to a knee brace. More particularly, it relates to a hinged leg brace for alleviating problems with rotation and subluxation of a tibia with respect to a femur in the leg of a wearer.

DESCRIPTION OF THE PRIOR ART

A wide variety of approaches have been employed in braces for the leg and the like. Thus, for example, reference may be had to U.S. Pat. Nos. 618,097; 1,228,113; 2,144,641; 2,308,776; 3,528,412; 3,581,741 and 3,669,105 for various types of knee braces for protection of knee joints or the like. None of these prior art braces have been totally satisfactory in preventing or alleviating problems with rotation of the tibia with respect to the femur as a primary problem; or subluxation of the tibia with respect to the femur. A germain invention was described and claimed in a co-pending application Ser. No. 227,381 entitled "BRACE FOR ARTICULATED LIMBS," Bledsoe, filed Jan. 22, 1981, assigned to the assignee of this invention; and the contents of that application are incorporated herein by reference for details that are omitted herefrom. A good review of the prior art as shown in U.S. patents and in general employed in the past was contained therein. A portion of that material will be repeated herein to give the reader an understanding without requiring reference to another instrument. Doctors and other health technicians frequently impose restraints on a person's bones, joints and connective tissue to allow natural healing process to be started or completed before restraints are released or broadened. Broadening allows additional movement and alleviates problems with atrophying of the muscles or the like. The new thinking is apparently to eliminate as much as possible of the bulky conventional casts and to wear temporary apparatus that can be removed to prevent problems with skin maceration, to accomodate changes as healing of the injury takes place and to allow better attention to personal hygiene and the like.

In that file history, there were discussed groupings of knee braces and like ranging from the immobilizers which did not have a hinge and are not really pertinent and not discussed herein; through braces that are relatively permanent for long term wear; such as, those disclosed in U.S. Pat. Nos. 2,632,440; 2,943,622; 3,826,251; 3,827,431; and 3,844,279. These long term braces did not have the rotation and subluxation control wedge and cuffs of this invention. Typical of the apparatus that employs a hinge with knee braces are those shown in the following U.S. Pat. No. 3,575,166 describes apparatus in which two rigid cuffs partially encircle a person's thigh and calf, respectively, encompassing about 270° of the wearer's leg member and employing a flexible elastomeric material to fill in the remaining 90° gap. A single hinge is rigidly connected on each side of the thigh and calf cuffs in order to provide some control with regard to a person's knee movements. U.S. Pat. No. 3,581,741 discloses similar "body" portions 18, 28 which are described as being a tough polymeric plastic material which may be internally reinforced with glass fibers and the like. U.S. Pat. No. 3,669,105 discloses a construction which has the advantage of being manufactured and worn by athletes having weakened knees. U.S. Pat. No. 3,785,372 describes a relatively complicated hinge apparatus. U.S. Pat. No. 3,786,804 describes apparatus having a single piece cylindrical sleeve of elastic material with loosely fitting pockets. U.S. Pat. No. 4,220,148 discloses a stabilizer but does not disclose the aspects of this invention. U.S. Pat. No. 4,233,967 discloses a plastic construction for attaching pairs of elongated braces but does not have the structure of this invention. U.S. Pat. No. 4,241,730 discloses a knee support with includes a pair of pivotally interconnected rigid braces but does not include the structure of this invention; U.S. Pat. No. 4,271,831 describes a knee brace having upper and lower sections that encase the proximal and distal members of the leg and have a hinge therebetween but do not have the structural features of this invention.

It has been found desirable that the knee braces such as are the subject of this invention have the following features not heretofore provided by the prior art:
1. The brace should have a posterior thigh cuff and an anterior calf cuff; whereas most of the prior art braces have had posterior thigh and calf cuffs.
2. The respective metal cuff should be allowed some slight pivotal motion.
3. The condyle pads should be elongated and have straps that are different from the usual design so as to alleviate the usual problems with brace wearing; that is, having the strap hanging on the knee and displacing the brace with movement of the knee.
4. The brace and calf cuff should have a wedge shape designed to fit the anatomical cross-section of the normal human leg to stop rotational subluxation of the tibia on the femur. This will obviate relying on elastic straps that grasp the leg with an inherent tightness of the strap and frictional attachment to the skin and obviate the necessity for derotation straps.
5. The knee brace should provide a direct mechanical block to anterior mobility of the tibia on the femur.
6. The knee brace should restrict medial and lateral of varus and valgas mobility of the tibia on the femur.

SUMMARY OF THE INVENTION

Accordingly, it is an object of this invention to provide a knee brace that alleviates the deficiencies of the prior art, particularly with respect to the rotation and subluxation of the tibia with respect to the femur and that provides one or more of the features delineated hereinbefore and not heretofore provided by the prior art.

It is a specific object of this invention to provide a lightweight knee brace that can be readily removed or adjusted and alleviating problems with swelling, muscle atrophy, hygiene as well we providing all of the features not heretofore provided by the prior art.

These and other objects will become apparent from the descriptive matter hereinafter, particularly when taken in conjunction with the appended drawings.

In accordance with one embodiment of this invention, there is provided a knee brace for alleviating problems with rotation and subulxation of the tibia with respect to the femur in the leg of a wearer, including:
a. first and second pairs of elongate braces, with each of the braces being relatively stiff so as to resist both torsion and beinding loads, the first pair of elongate braces being adapted to lie on opposite sides of the wearer's thigh and second pair of elongate braces being adapted to lie on opposite sides of the wearer's calf;

b. a pair of respective hinge means connected respectively with the first and second pairs of braces at their respective central ends for allowing controlled flexion and extension of the wearer's leg; and c. means for adjustably placing and holding the respective pairs of elongate braces in the desired attained position on respective opposite sides of the wearer's thigh and calf with the hinge means positioned directly adjacent the wearer's knee; and the improved construction for alleviating problems with rotation and subluxation of the tibia with respect to the femur. The improvement is characterized by an anterior tibia cuff connected with the second pair of braces and having a flattened chord that is disposed and designed so as to ride against and grasp the tibia by its padding by being molded to the anatomical cross-section of the leg. Specifically, it rides against the leg at the inside anterior of the tibia for preventing rotation of the tibia and preventing mobility by inherent rigidity of the brace. In a preferred embodiment, there is provided a posterior femur cuff connected with the first pair of braces and adapted for firmly engaging the posterior of the thigh posteriorly of the femur and adapted to co-act with the anterior tibia cuff for preventing subluxation of the tibia with respect to the femur of the wearer. Straps are provided for forcing intimate engagement of the leg members with the respective anterior tibia and the posterior femur cuffs.

It is believed helpful to have a broad discussion of this invention before considering the detailed aspects. The knee brace attaches to the thigh proximally with a posterior metallic thigh cuff that encompasses the posterior, medial, and lateral aspects of the thigh, encompassing approximately 220 degrees of the circumference of the thigh. The metal cuff is lined with a soft liner to facilitate pressure against the skin. The anterior or front portion of the cuff is closed with an elastic stretch material which completes the circumference of the thigh, being attached to one side of the cuff and then being stretched tautly across the front of the thigh, grapsing the thigh in the cuff. This elastic stretch material then attaches back to itself with Velcro attachments. In this fashion the thigh is grapsed firmly. Descending from the proximal thigh cuff are two metal uprights, or braces, which run to a calf cuff. These braces are hinged to allow flexion and extension of the knee joint as discussed in more detail hereinafter. The thigh cuff has an attachment to the medial and lateral metal uprights with an off-set rivet which allows the thigh cuff to rotate through an arc of approximately 20 degrees on the metal uprights. This rotation between the thigh cuff and the metal uprights allows for minor adjustment in the position of the brace as the knee or leg goes through a range of motion. This stops the brace from cutting into the skin of the thigh as more rigidly adherent braces do.

Descending from the thigh cuff the two metal uprights run on the medial and lateral aspects of the knee. They are contoured to the shape of the leg in their design. Each brace, right or left, is of the design for the right or left knee specially. The uprights are hinged with a hinge that has a cam design which allows the brace to flex and extend following the normal articulated cam effect of a normal knee joint. On the inner aspect of each hinge is a condyle pad. This is made of a soft elastic material or rubberized material. It rests against the medial and lateral femoral condyles of the knee and holds the brace in place at the knee level. There are straps that run from the upper and lower portions of the condyle pad. One runs above the patella across the front of the knee and the lower one runs below the level of the patella at the level of the tibial tubercle or the insertion of the patella tendon. This lower strap has been moved inferiorly so that flexion and extension does not cause the strap to be a leverage to push the brace down on the leg as the patella or kneecap travels over the front of the knee. The condyle pads are fixed by a rivet type attachment to the inner aspect of the hinges. The lower portion of the metal uprights then connects with an off-set rivet, again allowing approximately 20 degrees of rotation, to the anterior calf cuff. This cuff is metal, again is of semi-circular design, in its outer aspect encompassing approximately 220 degrees of the circumference of the leg. It is enclosed posteriorly by an elastic stretch strap that is attached to one side of the metal cuff, stretches across the back of the calf, and then re-attaches to itself around the cuff with a Velcro attachment, thereby gaining a firm grasps on the leg below the knee joint.

The anterior calf cuff is unique on its inner aspect in its design. There is a soft material insert which is a sponge rubberized material, soft to avoid irritation on the skin and bony prominences. The shape of the inner aspect of the cuff is a flattened chord designed to fit its flat surface medially on the subcutaneous border of the tibia so that it can gain purchase to the subcutaneous border. The outer aspect rounded to rest against the rounded aspect of the anterior tibial compartment anteriorly. The posterior calf is then encompassed with an elastic stretch band posteriorly. In this fashion, the unique flattened chord design grasps the leg firmly by its anatomical configuration.

This knee brace is manufactured in six different sizes in its commercial embodiment so that a close anatomical fit of any leg can be achieved.

DESCRIPTION OF PREFERRED EMBODIMENT(S)

This invention will be described as employed in allowing the healing of a leg injury and preventing rotation and subluxation of the tibia with respect to the femur of the leg; although it may be useful in other applications.

Figure 1:
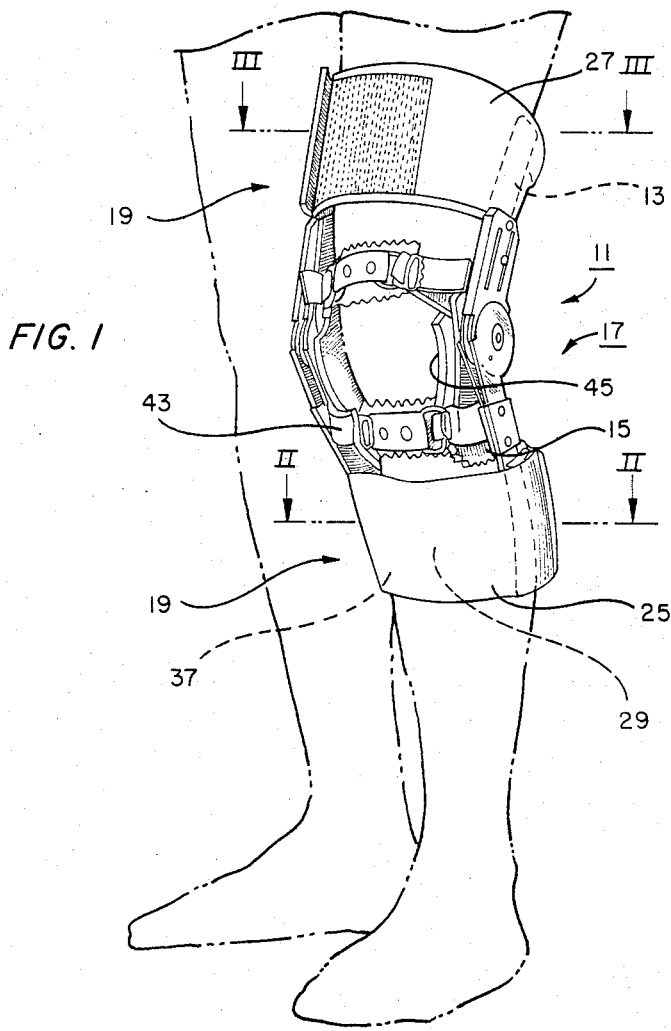
FIG. 1 is an isometric view showing one embodiment of this invention.

Referring initially to FIG. 1, the knee brace 11 is illustrated for controlling the degree of motion which is permitted by a wearer's distal member with respect to the proximal member while controlling rotation and subluxation of the tibia with respect to the femur. The knee brace 11, FIGS. 1 and 4, includes first and second pairs of uprights, or braces 13, 15 hinge means 17 and means 19 for adjustably placing and holding the respective pairs of elongate braces 13, 15 and hinge means 17 in a desired correct attained position on opposite sides of the thigh, knee and calf of the wearer.

Each of the braces is relatively stiff so as to resist both torsion and bending forces, or loads. A preferred structural material for the core of the brace is an elongate piece of aluminum having pre-determined width and thickness; for example, about 2 centimeters wide and about 3 millimeters thick. The respective braces have their central ends, 21, 23 connected with their respective hinge means 17. The braces are adapted to be positioned on opposite sides of the wearer's thigh and calf. As illustrated, the first pair of braces are adapted to be emplaced on respective sides of the wearer's thigh 22 and second pair of braces are adapted to be emplaced along respective sides of the wearer's calf 24.

Any other structurally strong bracing material can be employed. The type braces employed in the prior art may be employed herein and the respective braces, whether or not they employ Velcro material for being held in place, will depend on the type of means 19 for holding in place and on the hinge means 17.

The hinge means 17 may comprise any of the satisfactory hinge means of the prior art. Preferably, the hinge means 17 will be a complex hinge that is able to accommodate simulated motion of an actual knee requiring a compound center of rotation, such as described in a co-pending application entitled "KNEE BRACE HINGE", Ser. No. 473,229, (DF-448), inventor Kelsey (no middle initial) Martin, filed 3/8/83 and assigned to the assignee of this invention; and the descriptive matter of that patent application in incorporated herein by reference for details that are omitted herefrom. In that application, there was disclosed means for limiting the degrees of pivotal movement in extension and flexion of the calf with respect to the thigh, and hence of the tibia with respect to the femur. Specifically, the hinge means of that application had indices and an indicator that could be screwed to limit the range of motion that the wearer would have. Of course, other types of hinges have been known in the prior art and as long as they are satisfactory to the doctor employing the knee brace of this invention, they may be employed. As described in the aforementioned patent application, Ser. No. 227,381 "BRACE FOR ARTICULATED LIMBS", the type of hinge means is not critical to this invention. It should be compatible with the means 19 for holding the braces in place, however.

The means 19 for placing and holding the braces in a correct desired attained position may comprise any of the means employed heretofore in the prior art that are satisfactory with the objects delineated herein and not at conflict with preventing rotation and subluxation of the tibia with respect to the femur. It is necessary that the means be adequate to hold the respective pairs of elongate braces in a desired attained position on the respective opposite sides of the thigh and calf of the wearer with a hinge means correctly positioned adjacent the wearer's knee. One embodiment is that described in the aforementioned Ser. No. 227,381 and the application "KNEE BRACE HINGE", Ser. No. 473,229 (DF-448). In those applications, the means included a flexible sheet of cushion material that is adapted for being wrapped snugly around the wearer's thigh and around the wearer's calf with a preferred type of flexible material being medium density, open cell polyurethane foam having a thickness of about three-eighth (⅜) inch. In this invention, it is preferable not to employ the sheet material since more direct engagement of the respective knee and tibia wedge can be effected without the sheet material. In this invention, the means 19 includes at least respective elastic straps 25 for completing encirclement of the calf of the wearer and 27 for completing encirclement of the thigh of the wearer. These straps, thus, complete encirclement of the respective calf and thigh and fold back to fasten to themselves with Velcro tabs. The calf strap 25 holds the padded flattened chord firmly against the leg at the inside anterior of the tibia so that the specially designed tibia flattened chord is held in place to gain purchase for rotation control on the subcutaneous border of the tibia.

In like manner, the thigh strap 27, by completing encirclement of the thigh of the wearer ensures that the posterior cuff is brought into intimate engagement with the leg posteriorly of the femur. The advantages of this intimate engagement will be delineated later hereinafter with respect to the anterior tibia of cuff 29 and the posterior femur cuff 31.

Figure 2:
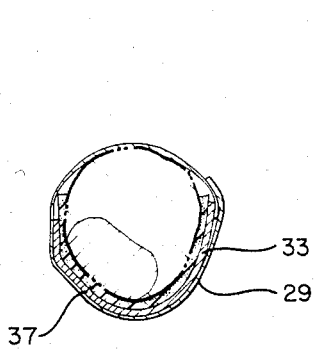
FIG. 2 is a partial cross-sectional view taken along the line II—II of FIG. 1.
Figure 4:
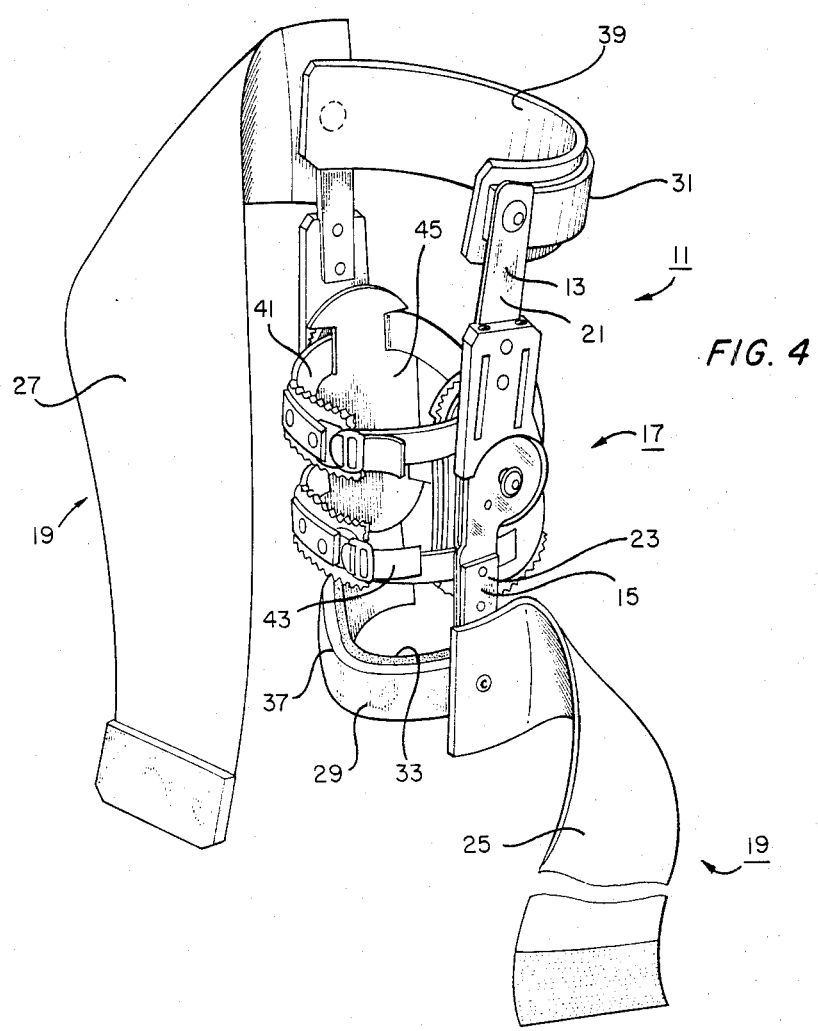
FIG. 4 is an isometric view of the knee brace of FIG. 1.
Figure 5:
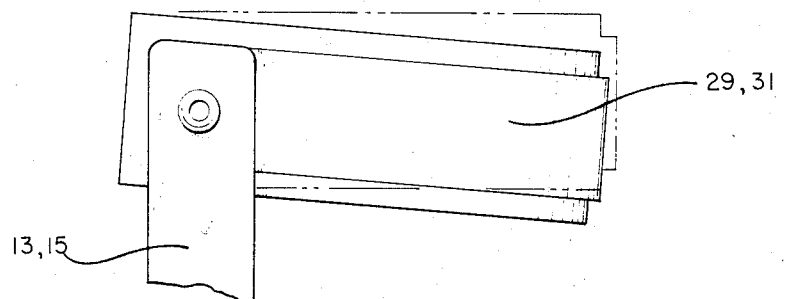
FIG. 5 is a partially side elevational view of the connection of the cuffs with the respective braces, allowing slight pivotal motion.

The primary improvement in this invention comprises the use of a special anterior cuff 29, FIGS. 1, 2 and 4, connected with the second pair of braces 15 and adapted to engage the anterior portion of the leg at the anterior interior of the tibia. As can be seen, the cuff 29 has a padded internal section 33, FIGS. 2 and 4, and comprises a flattened chord 37. The flattened chord is connected with the anterior cuff 29 and is designed to gain purchase for rotation control on the subcutaneous border of the tibia; and, hence, prevent or control rotational movement of the tibia with respect to the femur. As illustrated, the flattened chord is an integral part of the band 35 of the cuff 29. As can be seen in FIG. 5, a slight pivotal motion of about 20° is allowed the cuff to prevent digging into the flesh when being worn.

Moreover, the anterior cuff 29 being on the anterior portion of the tibia co-acts with the posterior cuff 31 on the thigh to prevent subjuxation of the tibia with respect to the femur.

The posterior cuff 31 is allowed the slight pivotal motion of about 20°, also, to prevent digging into the flesh.

Figure 3:
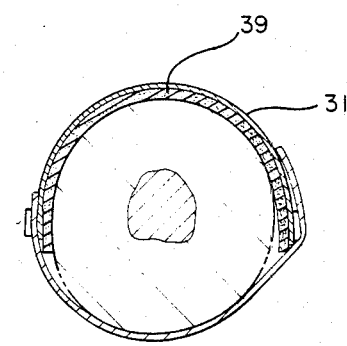
FIG. 3 is a partial cross-sectional view taken along the line III—III of FIG. 1.

The posterior cuff 31 also has an interior pad 39, FIGS. 3 and 4, for being brought into intimate contact with the posterior portion of the thigh posteriorly of the femur and is adapted for firmly engaging the posterior portion of the thigh. The posterior cuff is connected with the first pair of braces and co-acts with the strap 27 to maintain intimate engagement with the thigh and in co-action with the anterior cuff 29 on the anterior of the tibia, alleviate problems with subluxation of the tibia. The materials of construction of the respective cuffs are those generally employed in this art and will comprise plastic material that can be readily cleaned. The padded portion will preferably comprise the cleanable plastic foam, such as the polyurethane or the like. Preferably, a plurality of tabs of the hook-type fastening material, commercially available under the name of Velcro, will be employed for effecting intimate positioning and engagement of the respective element for holding them in place.

The straps that are employed may be non-elastic or may be stretchable with a relatively high co-efficient of elasticity as long as they have the desired strength and lack of resiliency to hold the braces in place. Preferably, the straps will be wide for comfort and have adequate strength in order to ensure that there is no risk of failure such as might be occasioned by unusual flexing of the muscle or unexpected load caused by an accidental fall or the like. The straps may be secured by the respective D-rings at the ends of with respective pieces of Velcro resilient hook material to create the desired tension and holding in place of the respective braces and/or cuffs.

Additional straps, such as upper strap 41 and lower strap 43, FIGS. 1 and 4, can be employed if desired. Upper strap 41 runs across the upper portion of the condyle pad on the knee hinge. Specifically, the upper strap 41 runs above the patella across the front of the knee. The lower strap 43 runs from the lower portion of the condyle pad. Specifically, the lower strap 43 runs below the level of the patella at the level of the tibial tubercle, or the insertion of the patella tendon. This lower strap has been moved inferiorly so that flexion and extension does not cause the strap to be a leverage to push the brace down on the leg as the patella, or kneecap, travels over the front of the knee.

In operation, the knee brace 11 is applied to the patient's leg as described hereinbefore. For example, the leg may be inserted intermediate the lower anterior cuff 29 and the posterior cuff 31 and the hinge positioned adjacent the knee. Thereafter, the respective straps may be tightened to hold the knee brace in place with the padded flattened chord 37 held interior and anterior of the tibia and brought into firm engagement with the leg portion on the subcutaneous border of the tibia and the strap 25 tightened in place. The posterior cuff 31 is then tightened in place with its respective strap such as strap 27. As many supplemental straps as are needed can be employed. If limited movement of the hinge means is to be employed, the adjustments are made to the hinge means to control movement of the desired degrees of flexion and extension. For example, as set forth in the aforementioned "KNEE BRACE HINGE", Ser. No. 473,229 (DF-448), the indicators and plungers are set by screwing the nuts with an Allen wrench or the like to obtain the desired limit on flexion and extension of the leg.

As implied hereinbefore, the respective means 19 can be removed at will; for example, replaced with a new tighter fit if swelling should decrease and the apparatus begins to feel loose. Unlike previous types of permanent casts and the like, the knee brace 11 can be easily and quickly adjusted, removed for hygiene or the like. The straps are easily tightened or removed. In fact, the entire assembly on a leg will usually take 5 minutes or less.

Moreover, the weight of this invention is less than one-half to that ordinarily employed.

From the foregoing, it can be seen that this invention accomplishes the objects delineated hereinbefore.

Specifically, this invention provides the following features not heretofore provided in the prior art:
(1) The brace has a posterior thigh cuff and an anterior calf cuff; whereas, most other prior art braces have had posterior thigh and posterior leg cuffs.
(2) The attachment of the metal cuff to the metal uprights is by an off-set or rivet hinge that allows a 20° arc of motion to allow the brace to conform to the leg position with movement without digging into the flesh.
(3) The hinge is a unique design that follows the anatomical cam mobility of the knee.
(4) The condyle pads are elongated and the straps are different from the usual design in that the inferior strap is placed lower on the leg than most other straps. This positioning of the strap stops the usual problem with brace wearing; that is, the strap hanging on the kneecap and displacing the brace with movement of the knee.
(5) The brace has a unique inferior, or calf cuff, in that the aspect of the calf cuff has a padded flattened chord shape that has been designed to fit the anatomical cross-sectional shape of the normal human leg. This calf cuff allows a firm purchase of the inferior portion of the brace on the leg. One of the primary purposes of this brace is to stop rotational subluxation of the tibia on the femur. Most other braces rely on elastic straps grasping the leg by inherent tightness of the strap and frictional attachment to the skin. They also rely on derotation straps that are straps which run across the leg in a criss-cross fashion, again gaining their purchase on the skin by friction. This unique brace gains its purchase on the leg by conforming to the anatomical bony outline and soft tissue outline of the leg.
(6) Unlike most other braces that have a posterior thigh and a posterior calf cuff, this brace inhibits anterior subluxation of the tibia on the femur by having a posterior thigh cuff and an anterior leg cuff. The anterior leg cuff is thus a direct and mechanical block to any anterior mobility of the tibia on the femur.
(7) Medial and leteral of varas and valgus mobility of the tibia on the femur is restricted by the nature of the medial and lateral hinged uprights, or braces.

Although this invention has been described with a certain degree of particularity, it is understood that the present disclosure is made only by way of example and that numerous changes in the details of construction and the combination and arrangement of parts may be resorted to without departing from the spirit and the scope of the invention, reference being had for the latter purpose to the appended claims.

What is claimed is:

1. A knee brace for alleviating problems with tibia rotation and tibia desubluxation with respect to the femur of respective proximal and distal members of a wearer, comprising:
   a. first and second pairs of elongate braces with each of said braces being relatively stiff so as to resist both torsion and bending forces; said first pair of braces being adapted to lie on opposite sides of the wearer's thigh and said second pair of braces being adapted to lie on opposite sides of the wearer's calf;
   b. a pair of respective hinge means connected respectively with said first and second pairs of braces at their respective central ends for allowing controlling flexion and extension of the wearer's leg, and
   c. means for adjustably placing and holding respective pairs of elongate braces desired attained positions on respective opposite sides of the wearer's thigh and calf with said hinge means positioned correctly adjacent the wearer's knee;
the improvement comprising:
   d. an anterior cuff connected with said second pair of braces on opposite sides of the wearer's calf and having a flattened chord that is disposed so as to ride against the leg at the inside anterior of the tibia for preventing rotation of the tibia.

2. The knee brace of claim 1 wherein said flattened chord is padded on its inside surface that contacts the leg at the inside anterior of the tibia.

3. The knee brace of claim 2 wherein a strap is provided for completing encirclement of the wearer's distal member and holding the flattened padded chord firmly against the leg at the inside anterior of the tibia.

4. The knee brace of claim 2 wherein a posterior cuff is provided for the posterior portion of the proximal member of the wearer; said cuff being connected with said first pair of braces and firmly engaging the posterior of the thigh for co-acting with said anterior cuff and preventing subluxation of the tibia with respect to the femur of the wearer.

5. The knee brace of claim 4 wherein a strap is provided for completing encirclement of the wearer's proximal member and holding said posterior cuff firmly against the leg at the posterior of the femur.

6. The knee brace of claim 5 wherein a strap is also provided for completing encirclement of the wearer's distal member and holding the flattened chord firmly against the leg at the inside anterior of the tibia.

7. A knee brace for alleviating problems with tibia rotation and tibia desubluxation with respect to the femur of proximal and distal members of a wearer, comprising:
   a. first and second pairs of elongate braces with each of said braces being relatively stiff so as to resist both torsion and bending forces; said first pair of braces being adapted to lie on opposite sides of the wearer's thigh and said second pair of braces being adapted to lie on opposite sides of the wearer's calf;
   b. a pair of respective hinge means connected respectively with said first and second pairs of braces at their respective central ends for allowing controlling flexion and extentions of the wearer's leg; and
   c. means for adjustably placing and holding respective pairs of elongate braces at desired attained positions on respective opposite sides of the wearer's thigh and calf with said hinge means positioned correctly adjacent the wearer's knee;
   the improvement comprising:
   d. a posterior cuff connected with the first pair of braces and adapted for firmly engaging the thigh of the wearer posteriorly of the femur and above the hinge means; and an anterior band connected with the second pair of braces below the hinge means and having a flattened chord that is disposed so as to ride against the anterior of the the tibia for preventing rotation and desubluxation of the tibia with respect to the femur of the wearer; said flattened chord having a padded inside surface that contacts the leg at the inside anterior of the tibia; said anterior band being adapted for completing encirclement of the wearer's distal member and holding the flattened padded chord firmly against a leg at the inside anterior of the tibia.

* * * * *